(12) United States Patent
Bond-Thorley et al.

(10) Patent No.: US 9,372,174 B2
(45) Date of Patent: Jun. 21, 2016

(54) ULTRASONIC INSPECTION TOOL

(75) Inventors: Andrew Bond-Thorley, Bristol (GB); Richard Freemantle, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 255 days.

(21) Appl. No.: 13/881,382

(22) PCT Filed: Oct. 20, 2011

(86) PCT No.: PCT/GB2011/052031
§ 371 (c)(1),
(2), (4) Date: Apr. 25, 2013

(87) PCT Pub. No.: WO2012/056218
PCT Pub. Date: May 3, 2012

(65) Prior Publication Data
US 2013/0233082 A1    Sep. 12, 2013

(30) Foreign Application Priority Data
Oct. 29, 2010  (GB) .................... 1018259.0

(51) Int. Cl.
*G01N 29/22* (2006.01)
*G01N 29/04* (2006.01)
(Continued)

(52) U.S. Cl.
CPC ............ *G01N 29/225* (2013.01); *G01N 29/043* (2013.01); *G01N 29/265* (2013.01); *G01N 29/28* (2013.01); *G01N 2291/106* (2013.01); *G01N 2291/2638* (2013.01); *G01N 2291/2694* (2013.01)

(58) Field of Classification Search
CPC ... G01N 29/225; G01N 29/28; G01N 29/043; G01N 29/265; G01N 2291/2694; G01N 2291/2638; G01N 2291/106
USPC .................... 73/644, 625, 628, 640, 643, 661
See application file for complete search history.

(56) References Cited

U.S. PATENT DOCUMENTS 3,946,599 A * 3/1976 Patt ........................ G10K 11/02
                                                                310/336
5,067,352 A   11/1991 Floret
5,915,277 A * 6/1999 Patton ................ G01N 27/9033
                                                                73/601
(Continued)

FOREIGN PATENT DOCUMENTS

GB           2303704 A       2/1997
GB   WO 9705479 A1 *  2/1997 ............. G01N 29/24
(Continued)

OTHER PUBLICATIONS

International Search Report and Written Opinion issued on Dec. 16, 2011 for PCT/GB2011/052031.
(Continued)

*Primary Examiner* — Laura Martin
*Assistant Examiner* — Suman K Nath
(74) *Attorney, Agent, or Firm* — Hauptman Ham, LLP

(57) ABSTRACT

An ultrasonic inspection probe comprising: a flexible ultrasonic array, a flexible coupling component arranged to ultrasonically couple the flexible ultrasonic array to a workpiece at a coupling boundary surface, a loading component arranged to apply a pressure to the coupling component to a surface opposite the coupling boundary surface to maintain contact between the coupling boundary surface and a workpiece.

14 Claims, 3 Drawing Sheets

Figure 1:
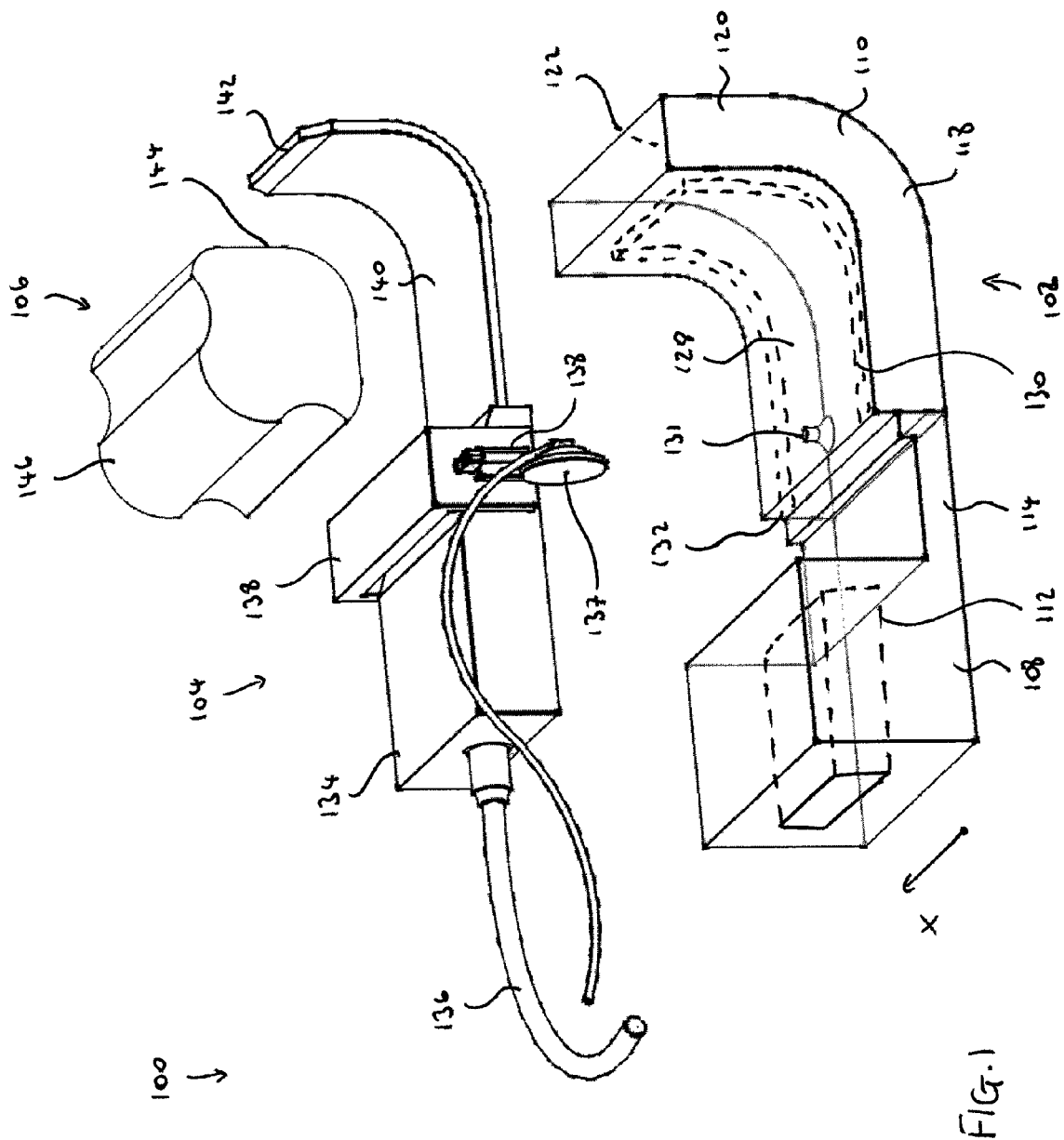

(51) Int. Cl.
*G01N 29/265* (2006.01)
*G01N 29/28* (2006.01)

(56) References Cited

U.S. PATENT DOCUMENTS

| | | | |
|---|---|---|---|
| 6,298,727 | B1 | 10/2001 | Fleming et al. |
| 8,151,643 | B2 * | 4/2012 | De Smet ................ G01H 11/08 73/587 |
| 2008/0314154 | A1 * | 12/2008 | Fetzer ................ G01N 29/2468 73/638 |
| 2010/0236330 | A1 * | 9/2010 | Nyholt ................ G01N 29/223 73/644 |

FOREIGN PATENT DOCUMENTS

| | | | | |
|---|---|---|---|---|
| GB | WO 2010010317 | A1 * | 1/2010 | ........... G01N 29/221 |
| JP | 2007192649 | A | 1/2006 | |
| WO | WO 9705479 | A1 * | 2/1997 | |
| WO | 2009130216 | A1 | 10/2009 | |
| WO | 2010010317 | A1 | 1/2010 | |
| WO | WO 2010010317 | A1 * | 1/2010 | |

OTHER PUBLICATIONS

Intellectual Property Office Search Report issued on Jan. 31, 2011 in GB Application No. 1018259.0.

* cited by examiner

ULTRASONIC INSPECTION TOOL

RELATED APPLICATIONS

The present application is a National Phase of PCT/GB2011/052031, filed Oct. 20, 2011, and is based on, and claims priority from, Great Britain Application No. 1018259.0, filed Oct. 29, 2010.

The present invention is concerned with an ultrasonic inspection tool. More specifically, the present invention is concerned with an ultrasonic inspection tool which utilises a flexible array in order to account for variability in the dimensions of radiused components.

By radiused components, we mean components having a curved or circle-segment cross-section. Such components often comprise a radiused portion extending through 90 degrees with a planar flange extending from either end thereof, perpendicular to each other. Aircraft components such as stringers and wing spars are radiused components.

Composite radiused components may experience various defects within the radius. For example, fibre waviness and excessive porosity may detrimentally affect the mechanical properties of the material. As such, increase in material thickness has to be designed-in to account for this which increases the weight and cost of the component.

Traditional methods of detecting such flaws involve providing a rigid curved array of ultrasonic elements directed normal to the surface of the component in order to detect any flaws therein.

In many applications, and in particular in the aerospace sector, both the radius of the component and the "opening angle" (i.e. the angle between the flanges extending from either end of the radiused portion) varies along the length of the component. This may occur intentionally due to the shape of the component, or unintentionally due to manufacturing tolerances. Either way, this often causes problems for known array probes because variations in the dimensions of the component may produce inaccurate results as the ultrasonic pulses do not enter and exit the material in the expected manner.

In addition, should a user wish to inspect a wide range of radiused components with varying radii and opening angles, then generally that user has to use a different probe. This is expensive and means that a significant number of array probes must be kept in store to cope with variations in component dimensions.

It is an aim of the present invention to overcome, or at least mitigate, one of the above problems.

According to a first aspect of the present invention there is provided an ultrasonic inspection probe comprising:
  a flexible ultrasonic array,
  a flexible coupling component arranged to ultrasonically couple the flexible ultrasonic array to a workpiece, the flexible coupling component having a workpiece coupling surface and a loading surface opposite thereto,
  a loading component arranged to apply a pressure to the loading surface to maintain contact between the workpiece coupling surface and a workpiece in use.

According to a second aspect of the present invention there is provided a method of ultrasonically inspecting a workpiece comprising the steps of:
  providing a workpiece,
  providing a flexible ultrasonic array,
  providing a flexible coupling component,
  positioning the flexible coupling component at least partially between the array and the workpiece,
  applying a pressure to the array and/or the coupling component to ensure contact between the coupling component and the workpiece,
  ultrasonically scanning the workpiece using the flexible ultrasonic array.

Advantageously, the provision of such an inspection probe and method allows the user to maintain pressure in the direction of the workpiece such that the coupling component deforms and is thereby kept in constant contact with the workpiece. The material properties of the coupling component can be selected to ensure that equal pressure is maintained across the entire flexible array. Because the ultrasonic array probe is flexible, it deforms with the coupling component as the radius and/or opening angle of the workpiece changes.

In addition, the aforementioned assembly can be used on a wider range of component geometries thus eliminating the need for multiple probes.

Figure 2:
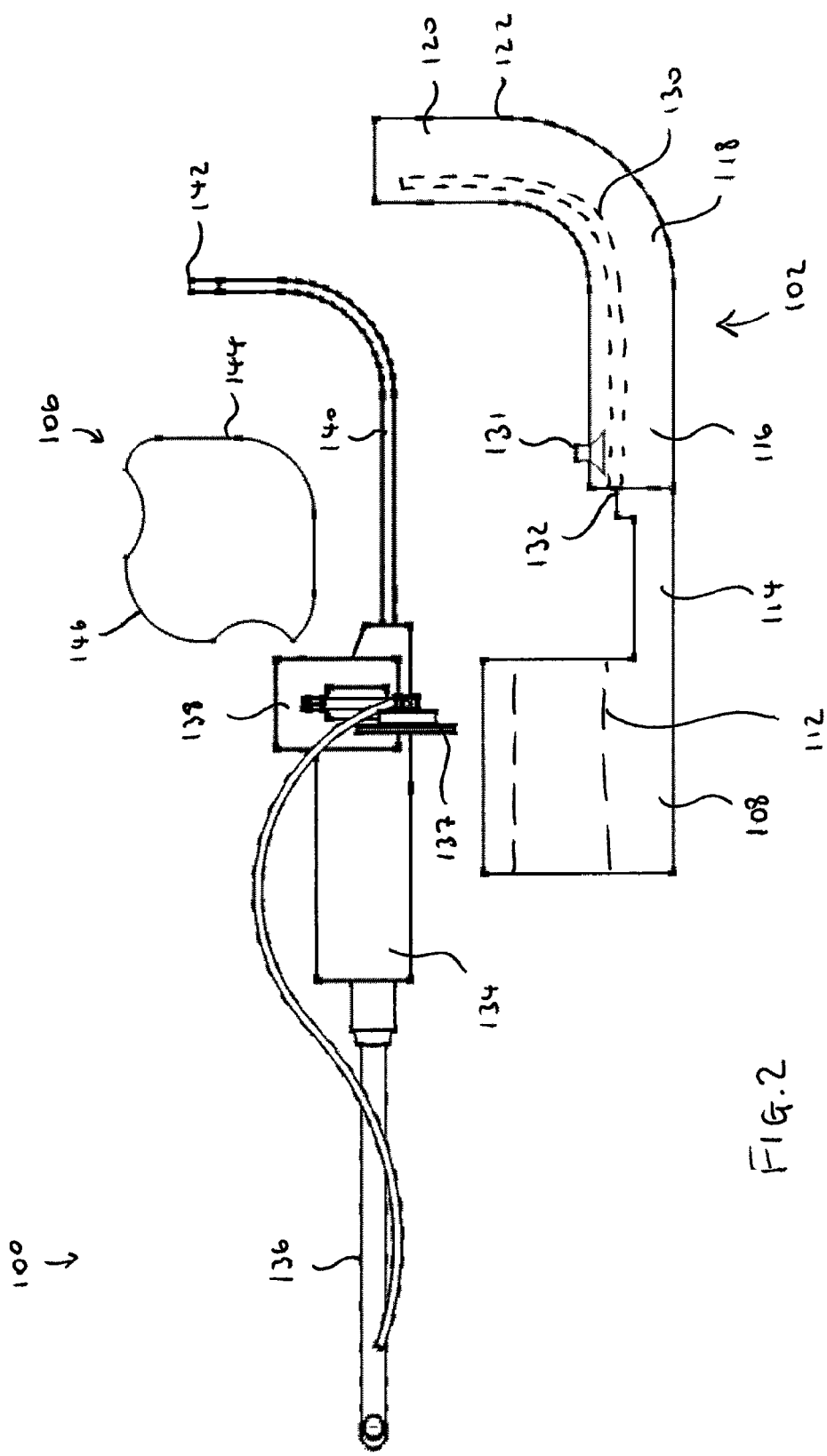
Figure 3:
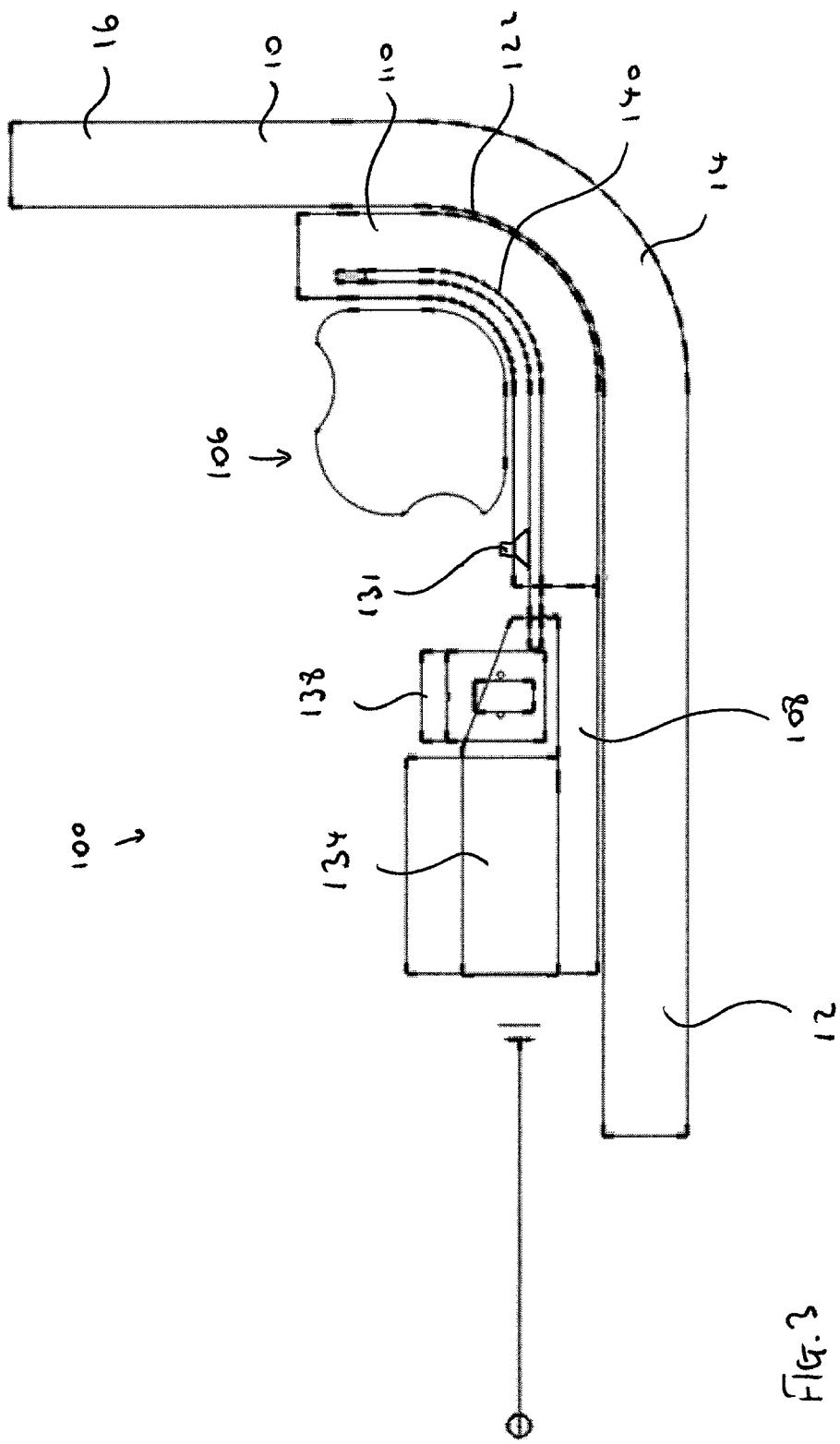

An ultrasonic inspection probe according to the invention will now be described in detail with reference to the accompanying drawings in which FIG. 1 is a perspective exploded view of an ultrasonic inspection probe according to the present invention;

FIG. 2 is an exploded side view of the ultrasonic inspection probe according to FIG. 1; and FIG. 3 is a side view of the ultrasonic inspection probe of FIG. 1 employed against a workpiece.

Referring to FIG. 1, an ultrasonic inspection probe 100 comprises a flexible coupling component 102, a flexible ultrasonic array probe 104, and a loading component 106.

The flexible coupling component 102 is generally prismatic, and has a substantially constant cross section along a first axis X. The flexible coupling component is constructed from a low ultrasonic attenuation clear silicone rubber. The flexible coupling component 102 comprises a mounting block 108 and a coupling part 110. The mounting block 108 is generally cuboid-shaped and comprises a probe body cavity 112 which is arranged to receive a probe body as will be described below. The mounting block 108 further defines a generally planar potion 114 which extends to meet the coupling part 110.

The coupling part 110 comprises a first leg 116 extending from planar part 114 of the mounting block 108. The first leg 116 is flat and planar. A radiused portion 118 extends from the first leg 116 to define a substantially 90 degree circle segment in cross-section which joins onto a second leg 120 extending at approximately 90 degrees to the first leg 116. In other words, the coupling part 110 comprises the first leg 116 with the second leg 120 perpendicular thereto and connected via a 90 degree radiused portion 118. The coupling part 110 is therefore suited for engagement with a similarly shaped workpiece.

The coupling part 110 defines a workpiece coupling surface 122 and a loading surface 124 opposite thereto. The coupling part 110 further comprises end surfaces 126, 128 perpendicular to the axis X.

Both of the workpiece coupling surface 122 and the loading surface 124 each define a first flat portion defined by the first leg, a second flat portion defined by the second leg 120 and a generally part-cylindrical surface area (radiussed section) defined therebetween.

The coupling part 110 defines an array probe slot 130 extending proximate and parallel to the loading surface 124 within the coupling part 110. The slot 130 extends from an open end 132 facing the mounting block 108. A valve 131 is in fluid communication with the slot.

The flexible ultrasonic array probe 104 comprises a probe body 134 connected to an ultrasound analysis system comprising a computer via a data connection 136 which carries the ultrasound signal. The probe body 134 further comprises an encoder mount 138 for mounting and connection to a rotary encoder 137. A flexible ultrasonic transducer array 140 extends from the probe body 134 and comprises a series of ultrasonic elements (not shown) which are spaced in a generally linear fashion from the region of the probe body 134 to a free end 142 of the ultrasonic transducer array 140.

The loading component 106 is a generally prismatic, semi-flexible, solid rubber block having a loading surface 144 which is substantially the same profile as the loading surface 124 of the flexible coupling component 102. The remaining surface of the loading component 106 which is not facing the flexible coupling component 102 is defined by an ergonomic hand grip 146.

Referring to FIG. 3, the ultrasonic inspection probe 100 is assembled as follows.

The encoder mount 138 is removed from the probe body 134 such that the probe body 134 can be inserted into the probe body cavity 112 in the mounting block 108. As the probe body 134 is inserted, the flexible ultrasonic transducer array 140 is slid into the slot 130 through the open end 132 within the coupling part 110 of the flexible coupling component 102. A vacuum pump is applied to the valve 131 to evacuate air from the slot 130 such that the sides of the slot 130 are in contact with the transducer array 140. The slot 130 is slightly wider than the array 140 such that all air is removed from the underside of the array 140 facing the coupling surface 122.

After insertion, the encoder mount 138 is reconnected to the probe body 134 and an appropriate encoder wheel 137 is attached to one or both sides of the encoder mount 138 such that it extends to the bottom surface of the planar part 114 and can contact a workpiece proximate thereto in order to detect the distance traveled along the workpiece by the ultrasonic inspection probe 100 in the direction of the axis X.

In use, the ultrasonic inspection probe 100 is positioned such that the workpiece coupling surface 122 is positioned proximate to and coupled with a workpiece 10.

The workpiece 10 comprises a first leg 12, a radius portion 14 and a second leg 16. A suitable coupling material such as a gel or water can be placed between the flexible coupling component 102 and the workpiece 10 to enhance coupling.

The ultrasonic array probe 104 can be activated and the ultrasonic inspection probe 100 moved along the workpiece 10 in a direction parallel to axis X. A detailed scan of the workpiece can be created in this manner.

As mentioned previously, the workpiece 10 may comprise variations in the opening angle (i.e. the angle between the first leg 12 and the second leg 16) and, in addition, the inside radius of the radius part 14 may vary. As the probe 100 is slid along the length of the workpiece 10 a user grips the loading component 106 and applies a force towards the radius part 14. This force will act to urge the workpiece coupling surface 122 of the flexible coupling component 102 against the workpiece 10 and its flexibility will account for any variation in opening angle or radius. As such, coupling between the flexible ultrasonic array probe and the workpiece 10 is maintained due to the flexibility of the flexible coupling component 102. Therefore, a reliable coupling and measurement can be made.

Variations fall within the scope of the present invention. For example, the arrangement may describe a concave workpiece coupling surface as opposed to a convex one. In addition, any shape of workpiece coupling surface such as wavy, flat, curved, may be used.

A positive air pressure may be applied to the valve 131 instead of a vacuum. In this scenario, the array 140 should form a close fit with the sides of the slot 130 such that as positive pressure is applied, the array 140 is pushed against the face of the slot 130 closest to the coupling surface 122. This will ensure good ultrasonic coupling is maintained.

The coupling component may be a water filled component constructed from a flexible membrane-like material. The coupling component will be generally the same size and shape as the coupling component 102.

This embodiment permits the use of slightly stiffer materials (the stiffness of which is offset by the fact that they are constructed as a structurally flexible membrane). Therefore lower friction materials can be used in this embodiment, making it useful in circumstances whereby the workpiece-silicon interface has a high coefficient of friction making scanning difficult.

Optionally, water may be fed into the water filled coupling component from a side other than the workpiece contact side, and several apertures created in the workpiece contact side to allow the water to escape. This provides additional lubrication and coupling for the movement of the component across the surface of the workpiece.

This approach is also useful for thin or weaker workpieces in which lower coupling forces must be used.

The invention claimed is:

1. An ultrasonic inspection probe for scanning a radiused workpiece comprising:
   a flexible ultrasonic array probe having:
      a probe body; and,
      a flexible ultrasonic transducer array extending from the probe body, the flexible ultrasonic transducer array comprising a series of ultrasonic elements extending towards a free end of the flexible ultrasonic transducer array;
   a flexible coupling component arranged to ultrasonically couple the flexible ultrasonic transducer array to the workpiece, the flexible coupling component having:
      a first leg, a second leg, and a radiused section therebetween; and
      a cavity defined therein
      a workpiece coupling surface; and,
      a loading surface opposite thereto, and,
   a loading component arranged to apply a pressure to the loading surface to maintain contact between the workpiece coupling surface and the workpiece in use;
      wherein the flexible ultrasonic transducer array is positioned at least partially within the cavity defined within the flexible coupling components such that the ultrasonic elements extend around the radiused section of the flexible coupling component to scan the radiused portion of the workpiece.

2. The ultrasonic inspection probe according to claim 1 in which the flexible coupling component and the ultrasonic array are mechanically coupled.

3. The ultrasonic inspection probe according to claim 1 in which the cavity comprise a slot.

4. The ultrasonic inspection probe according to claim 1 comprising a valve in fluid communication with the cavity, and arranged to permit introduction and/or removal of air from the cavity.

5. The ultrasonic inspection probe according to claim 1 in which the loading component is a hand-held block.

6. The ultrasonic inspection probe according to claim 1 in which the loading component defines a loading surface which is substantially the same shape as the loading surface.

7. The ultrasonic inspection probe according to claim 1 in which the flexible coupling component is a solid block of material.

8. The ultrasonic inspection probe according to claim 1 in which the flexible coupling component is constructed as a fluid filled membrane.

9. A method of ultrasonically inspecting a workpiece comprising the steps of:
   providing a radiused workpiece,
   providing a flexible ultrasonic array probe having:
      a probe body; and,
      a flexible ultrasonic transducer array extending from the probe body, the flexible ultrasonic transducer array comprising a series of ultrasonic elements extending towards a free end,
   providing a flexible coupling component having:
      a first leg, a second leg, and a radiused section therebetween; and,
      a cavity defined therein,
   positioning the ultrasonic array at least partially within the cavity of the flexible coupling component such that the ultrasonic elements extend around the radiused section of the flexible coupling component;
   applying a pressure to the array and/or the flexible coupling component to ensure contact between the flexible coupling component and the workpiece,
   ultrasonically scanning the workpiece using the flexible ultrasonic array.

10. The method of ultrasonically inspecting a workpiece according to claim 9 comprising the step of:
    altering the air pressure within the cavity to ensure coupling between the array and the coupling component.

11. The method of ultrasonically inspecting a workpiece according to claim 9 in which the step of altering the air pressure comprises the step of lowering the pressure in the cavity.

12. The method of ultrasonically inspecting a workpiece according to claim 9 comprising the steps of:
    providing a loading component,
    placing the array and the coupling component between the workpiece and the loading component,
    applying manual pressure to the loading component to compress the coupling component into the workpiece to increase contact therebetween.

13. The method of ultrasonically inspecting a workpiece according to claim 9 comprising the step of sliding the coupling component and array along the workpiece to progressively scan the workpiece.

14. The method of ultrasonically inspecting an aircraft component comprising the method of claim 9.

\* \* \* \* \*